(12) United States Patent
Misselbrook

(10) Patent No.: US 6,893,589 B1
(45) Date of Patent: May 17, 2005

(54) PROCESS FOR PRODUCING GRANULES

(75) Inventor: John Misselbrook, Southampton (GB)

(73) Assignee: Agform Limited, Southampton (GB)

( * ) Notice: Subject to any disclaimer, the term of this patent is extended or adjusted under 35 U.S.C. 154(b) by 0 days.

(21) Appl. No.: 09/889,827

(22) PCT Filed: Jan. 21, 2000

(86) PCT No.: PCT/GB00/00163

§ 371 (c)(1), (2), (4) Date: Nov. 28, 2001

(87) PCT Pub. No.: WO00/42846

PCT Pub. Date: Jul. 27, 2000

(30) Foreign Application Priority Data

Jan. 22, 1999 (GB) .............................. 9901479

(51) Int. Cl.$^7$ ............................................. B29C 47/00
(52) U.S. Cl. ........................ 264/115; 264/118; 264/128
(58) Field of Search ................................ 264/115, 117, 264/118, 128, 141, 142, 143

(56) References Cited

U.S. PATENT DOCUMENTS

| | | | | |
|---|---|---|---|---|
| 3,137,592 A | * | 6/1964 | Protzman et al. ............. | 127/71 |
| 3,159,505 A | * | 12/1964 | Burgess et al. ............... | 127/32 |
| 3,622,677 A | * | 11/1971 | Short et al. .................. | 514/778 |
| 4,065,289 A | * | 12/1977 | Judd ............................ | 504/313 |
| 5,075,058 A | * | 12/1991 | Chan et al. ................. | 264/118 |
| 5,443,764 A | * | 8/1995 | Lloyd et al. .................. | 264/15 |
| 5,474,971 A | * | 12/1995 | Sandell ........................ | 504/367 |
| 5,622,658 A | * | 4/1997 | Lloyd et al. .................. | 264/15 |
| 5,714,439 A | | 2/1998 | Houghton et al. | |
| 6,273,929 B1 | * | 8/2001 | Hobbs ....................... | 71/64.03 |

FOREIGN PATENT DOCUMENTS

| | | |
|---|---|---|
| DE | 24 03 427 | 8/1998 |
| EP | 484 147 | 5/1992 |
| GB | 1 339 005 | 6/1975 |
| GB | 1 433 882 | 4/1976 |
| WO | WO 89/00079 | 1/1989 |
| WO | WO9626828 | 9/1996 |

OTHER PUBLICATIONS

Pesticide Formulation and Adjuvant Technology, edited by Foy et al., 1996.
Poster presented at 2002 IUPAC Meeting of Basel by B. Delli Colli et al.
Advances in Pesticide Formulation Technology, H.B. Scher–ACS Symposium Series 254, Aug. 28–Sep. 2, 1983; pp. 186–187.
STAM$^R$ 80 EDF.
Leuenberger, et al., Theory of granulating–liquid requirement in the conventional granulation process, Pharmaceutical Technology International, Jul. 1979, pp. 35–42.
Leuenberger, Chapter 11 (part 2). Moist agglomeration of pharmaceutical powders (size enlargement of particulate materials)—the production of granules by moist agglomeration of powders in mixers/kneaders (pp. 377–389).
Westvaco brochure, "Pre–Mixes for Water Dispersible Granules" (1983).
Hovde, Water Dispersible Granules, presentation at symposium on pesticide Formulations and Applications Systems: 3rd Symposium, Oct. 11–14, 1982, Ft. Mitchell, KY.

* cited by examiner

Primary Examiner—Mark Eashoo
(74) Attorney, Agent, or Firm—Morgan, Lewis & Bockius LLP

(57) ABSTRACT

The invention relates to a process for the preparation of water-dispersible and water-soluble granules which exhibit superior properties in use while improving their ease and efficiency of manufacture. The process involves forming a particulate pre-mix of the components of the granule without forming a paste and extruding the pre-mix to form the granules.

17 Claims, No Drawings

PROCESS FOR PRODUCING GRANULES

This application is the National Phase of International Application PCT/GB00/00163 filed Jan. 21, 2000 which designated the U.S. and that International Application was published under PCT Article 21(2) in English.

This invention relates to a process for the production of granules. In particular water dispersible and water soluble granules. More particularly it relates to an extrusion process for the production of water dispersible granules. The invention is especially useful in the production of granules containing biologically active compounds and other substances and in particular, agrochemical products, for example pesticides.

Dispersible granule formulations of pesticides are known and have certain advantages. In particular, such granules are advantageous due to their ease of handling and reduced worker exposure compared to powder or liquid formulations and also due to their compatibility, comparative cost. Furthermore, environmentally friendly packaging may be used and the presence of inert materials also has environmental advantages. G. A. Bell, "Chemistry and Technology of Agrochemical Formulations", Edited by D. A. Knowles (Kluver, 1998), pages 80–114, describes a range of dispersible granule types and processes for their manufacture.

WO 89/00079 describes a process for the preparation of water dispersible granules which comprises mixing the desired ingredients of the granules to form an extrudable wet mix which has a dough-like consistency, that is, a consistency analogous to a stiff dough produced in the bread making process. Such dough-like consistency may be provided by thorough mixing on kneading using a mixing apparatus such as a pug mill, double shafted auger, or an extrusion apparatus may be adapted to provide suitable mixing. It also requires that after extrusion the wet extrusions are broken down by rolling, preferably in a tumbling action. However, the rolling action required following extrusion may cause the formation of a "shell" of compacted material on the outside of the granule that leads to an increase in the drying time/temperature. EP-A-00484 147 1 describes a process for preparing dispersible propanil granules. Propanils is N-(3,4-dichlorophenyl)propionamide. It is known that propanil may degrade during processing or have poor stability due to its low melting point. The process disclosed in EP-A-484 147 comprises the steps in sequence of combining one or more surfactants with propanil and milling to a particle size of less than 20 microns to form a premix, adding less than 25 percent by weight water and optionally a wetting agent to said premix and mixing until a paste is obtained granulating said paste thereby producing granules and drying said granules. This process is said to overcome certain difficulties in the processing of propanil due to its low melting point and tendency to become sticky during processing.

However, propanil, in addition to having a relatively low melting point, is also prone to hydrolysis. The formation of a paste containing water may lead to further difficulties as regards stability during processing if the energy input during the paste formation is too high. Thus, the above described processes may impose a number of constraints on the ingredients by limiting the choice of available components to those which are not heat sensitive which may be included in the granules due to the physical or chemical nature of those ingredients. In particular, the energy input required in the formation of the dough or paste may degrade certain low-melting, or temperature-sensitive, active materials. Water-soluble or slightly-soluble actives may form crystal bridges which, on addition to water, inhibit the rapid and desirably complete dissolution or disintegration of the granules to their primary particle size prior to granulation.

The handling of a dough or paste in a manufacturing plant can also cause processing problems. In particular difficulties may arise due to variation in the viscosity of the dough or paste caused by temperature and/or shear conditions. This factor may lead to variation in product quality and yield and may cause fouling or blockages in the process apparatus.

There remains a need for improvements to existing known processes of preparing granules that are dispersible and/or soluble in water to allow sensitive components to be included in formulations and to avoid or reduced processing problems for example due to fouling or blockage. Furthermore, granules providing excellent delivery of the active to the point of use including good dispersibility are desired. In addition physical properties such as ease of handling, low friability so as to reduce or minimise the dust content are also desirable for reasons of health and safety and ease of product distribution.

It has been found that acceptable granules may be produced by a process involving forming a pre-mix of the components of the granule and extruding the pre-mix provided that a paste is not formed during the preparation of the pre-mix which is to be extruded.

In a first aspect the invention provides a process for the production of water dispersible granules comprising, preparing a pre-mix in the form of a free-flowing powder, preferably a homogeneous powder, comprising an active material and an excipient and optionally other components, with at least one component of the pre-mix being liquid without forming a paste, and extruding the pre-mix in an extruder, for example a low pressure extruder to form the granules. The excipient may be liquid in which case an additional liquid components is not required although a further liquid component may be included as desired.

WO 96/25828 describes an apparatus and a method for extrusion which eliminates the undesirable effect of the ingress of pastes, which form as the moist finely divided, water-insoluble powders are forced through the screen of conventional, low-pressure extruders.

It has been surprisingly found that granules that are water-dispersible and/or water-soluble can be produced using the process according to the invention and they provide excellent delivery of the active to the crop to be treated. Further, the granules produced by a process according to this invention, exhibit improved characteristics as compared to granules formed by process of the prior art on storage, dilution and in use.

The process involves the initial preparation of a pre-mix comprising the active material together with at least one excipient in the form of a free-flowing, powder. Desirably the premix is a homogeneous powder. The pre-mix is preferably prepared by the absorption of a liquid for example water, or any other suitable liquid onto an active solid material, which is preferably finely divided. The active solid may be mixed with an excipient preferably a surfactant for example a dispersant and a wetting agent, a filter, a disintegrant, a stabiliser, a flow aid and the likeand mixtures thereof. It is especially preferred that the pre-mix comprises an active, an excipient comprising a dispersant and water. It is also preferred that the granule obtained from the process contains these components. In a preferred embodiment, the active materials is suitably milled either prior to the addition of the excipient or milled together with it.

Suitably the premix is formed by the application of shear especially in a blending step or a milling step and optimally in one or more blending steps and one or more milling steps. Suitable apparatus for the blending step(s) include a low-shear, high intensity blender such as a Lodige Ploughshare mixer ribbon. Y-cone, double cone or trough blender, so that a free-flowing powder is formed. The premix is fed directly or indirectly into a suitable low-pressure extruder, such as that described in WO 96/26828, so that the premix is compacted against the apertures in the screen and forced through. The composition of the premix and the extruder settings are such that the formation of a paste before extrusion is avoided. The powder premix which is fed to an extruder is converted into a compacted solid extrudate which can be collected as a free-flowing granule.

In the present process the material being processed remains a free flowing particulate material during the formulation of the pre-mix. In particular, the material does not form a paste prior to extrusion. However, as the composition contains one or more liquid components, it may be wet or dry provided that it remains free-flowing and particulate during the process. The particles of the material are of such a composition that they are able to move relative to one another and do not to any significant extent, agglomerate into lumps and remain as lumps having a particle size of at least several times that of the bulk of the particulate material being processed during the formation of the pre-mix. If any lumps are formed during this part of the process, the process conditions for formation of the premix and/or the composition of the premix should be varied so that the lumps disintegrate into finer particles on application of shear. If any such lumps or agglomerates are formed, it is especially preferred that the agglomerate is of such a composition and physical structure that it disintegrates into finer particles on the application of manual force by rubbing between the fingers.

In the context of the present invention, a paste may be considered as a mass of material, for example an agglomerate, which contains sufficient liquid or is at such a temperature that the particulate material being processed forms into an agglomerate which is mouldable or deformable and which is not free-flowing. Thus, a paste does not disintegrate into finer particles on application of shear, for example by rubbing between fingers, but rather remains as an agglomerated mass and the shear acts to mould or deform the agglomerate.

Depending on the components selected for producing the granules, the relative amounts of those components are selected and the process conditions for example the level of shear are selected so as to avoid the formation of a paste prior to extrusion.

After the extrusion step in the process, the granules so formed may be processed further as desired, for example by drying and by sewing or other size-classification steps. In a preferred embodiment of the invention, the granules are dried. The granules may be dried by any suitable equipment, for example, a fluid-bed drier and a tray dryer. As a further preferred process step, the granules are classified by size, for example, sieved so as to remove under- and over-sized material. In a preferred embodiment, the extruded material is suitably dried and size-classified. It is especially preferred that the process of the present invention does not involve a rolling process step in which the extruded material is treated.

In the process of the present invention, uniform, free-flowing granules are produced with excellent properties including uniform bulk density, lack of dust, resistance to attrition and rapid disintegration in water to form a suspension or solution of the active ingredient on use. In a preferred embodiment, over 90%, especially 99% of the granules, prior to sieving or screening, are of a suitable size such that further processing to alter the size of the granules is not required.

Avoiding the formation of a paste during the process prior to extrusion affords further advantages in that flexibility in the range of actives and other components which may be selected is increased as compared to processes in which a paste is formed. This permits the selection of actives and other ingredients which otherwise may not be suitable due to increasing processing difficulties. Thus any detrimental effects due to the formation of a paste on the ingredients, and vice-versa, are no longer a factor. Ingredients can thus be chosen that produce optimum product properties whether in use or otherwise, for instance in distribution, rather than the choice being compromised due to processing considerations.

The premix is suitably prepared by blending two or more materials, for example the active and the excipient and/or the liquid component, for a period of at least 30 seconds, preferably 1 to 15 minutes, more preferably 1 to 10 minutes and especially 2 to 5 minutes.

The solid component may be milled to an appropriate particle size prior to blending with other components. Preferably, milling is carried out after blending so the blended materials are milled to a desired particle size. Milling may be carried out by any suitable means although air milling is preferred. Suitably air milling is carried out at an air pressure of at least 2 bar and desirably at least 5 bar. Suitably, the milled material has a particle size of 2 to 30 microns and desirably 4 to 20 microns.

As desired one or more blending steps may be carried out after the milling step if desired. Such a blending step may be carried out for a least 30 seconds, preferably for 1 to 15 minutes and especially for 1 to 10 minutes. The one or more blending step may be carried out under low shear or desirably high shear conditions. Where more than one blending step is employed, it is preferred that the material being processed is subjected to high shear in the first blending step and low or moderate shear in a subsequent blending step.

The liquid component may be added to the milled material, either a blend or a single component product, or it may be added to a solid component in a blending step prior to or after the milling step. The liquid may be added in any suitable manner although it is preferred that the liquid be added as a spray in order to reduce the risk of agglomerates or lumps forming in the premix.

It is essential in the formation of the pre-mix that the steps in the formation are carried out under such conditions are for a period such that a paste is not formed.

The process may be employed to produce granules comprising a wide range of active ingredients. By way of example, the process of the invention may be employed to produce granules comprising, as the active, a pharmaceutical, an agricultural chemical, an oil field chemical, an animal feedstuff, a dyestuff, and a detergent. Granules comprising other types of active may also be produced by a process according to the invention. The process is particularly suitable for, but not limited to, the production of granules comprising an agricultural chemical.

Examples of agricultural chemicals which may be employed as the active include abamectin, imidazolinone, ametryn, attrazine, azoxystrobin, benomyl, bensulfuron-methyl, bentzone, bifenox, bromoxynil, captan, carbendazim, carfentrazone-ethyl, chloridazon, chlorothalonil, chlortoluron, chlorsulfuron, cinosulfuron, clodinafop, clopyralid, lambda-cyhalothrin, cyhexatin, cymoxynil, alpha-cypermethrin, deltamethrin, difluofenican, diflufican, dimethormorph, diuron, ethofumesate, emamectin benzoate, fibronil, glyphosate, imazamethabenz-methyl, imazapyr, imazethapyr, imadacloprid, isoproturon, linuron, mancozeb, maneb, metamitron, methiocarb, metribuzin, metasulfuron-methyl, milbectin, nicosulfuron, oxadixyl, oxyfluorfen, phenmedipham, pirimisulfuron-methyl, propanil, propyzamide, rimsulfuron, simzaine, sulfometuron,-methyl, thifensulfuron-methyl, thiram, tribenuron-methyl, and triflusulfuron-methyl.

Suitable excipients include surface active agents (surfactants) including wetting agents and dispersing agents or a combination of both and flow agents.

Examples of suitable wetting agents include: alkali metal, for example sodium salts of alkyl aryl sulphonates, alkyl aryl sulphosuccinates, and alkyl sulphates.

Examples of dispersing agents include sodium lignosulphonates, sodiumnaphthalene sulphonate formaldehyde condensates, tristyrylphenol ethoxylate phosphate esters, aliphatic alcohol ethoxylates, alkylphenol ethoxylates, copolymers, random and block of ethylene oxide and propylene oxide, "comb" graft copolymers are polyvinyl alcohol-vinyl acetate coplymers.

Suitable other excipients include disintegrants for example: Bentonite, modified starch and polyvinyl pyrrolidone:stabilisers, for example citric acid, polyethylene glycol and butylated hydroxy toluene; and fillers, for example, starch, lactose, china clay, sucrose and kaolin.

In addition to the active material and the excipient and liquid component, further ingredients, for example further excipients, may be fed to the process at any point, including before, during or after addition of the liquid component to the process, just prior to or during the extrusion step. However, if further ingredients are to be added, it is especially preferred that they be added to the process prior to extrusion and optimally be mixed with the active component prior to or with the addition of the liquid component. Suitable further ingredients include surfactants including dispersants and wetting agents, fillers, disintegrants, stabilisers and flow-aids. The important factor in the choice of a further ingredient and the amount of the ingredient is that it does not lead to the formation of a dough or paste during the process for example due to significant particle-to-particle interaction.

In an especially preferred embodiment of the invention, the active comprises propanil and the excipients comprise one or more of a disintegrant, a flow agent a filler and a surfactant. In a further preferred embodiment, the propanil is mixed with the disintegrant and flow agent, preferably by air milling, surfactant is then added to the mixture and then water is added to the mixture so as to form a free-flowing generally homogeneous powder, that is a particulate material. In an alternative embodiment, the propanil is blended with a surfactant, a disintegrant and a filter and then milled and water is added to the mixture after milling in a further blending step to produce a free-flowing generally homogeneous powder. The pre-mix powder is then extruded by passing through an extruder, preferably an extruder and extrusion process as described in WO 96/26828. The granules resulting from the extrusion process suitably have a thickness or particle size of 0.1 to 5 mm, preferably 0.3 to 2 mm and especially 0.5 to 1.5 mm. The granules are then suitably dried and optionally classified by sieving.

The invention provides a novel granular composition comprising an agricultural active and an excipient obtainable by a process according to the first aspect of the invention.

The invention is illustrated by the following examples but is in no way limited by them:

EXAMPLE 1

The following formulation was prepared:

| | |
|---|---|
| Propanil | 80% |
| Sodium alkyl aryl sulphonate | 1.0% |
| Sodium Lignosulphonate | 10.0% |
| Potato Starch | 1.0% |
| China Clay | to 100% |

The above formulation was prepared by first blending the Propanil Technical, china clay and starch in a Ploughshare blender for 5 minutes. The blend thus formed was then air milled to an average particle size of 5–7 microns. Water was added to the air milled premix in a Ploughshare blender until a water content of approx. 18% was obtained. Formation of a paste was avoided in preparing the premix. The free-flowing powder obtained was fed to a basket extruder. A low pressure extruder as set out in WO-A-96/26828 was used to extrude the premix. A compacted solid extrudate was obtained, which was dried at 65° C. for 15 minutes until a moisture content of below 1.5% was obtained.

The granules were tested as follows:

1 g of the granules were added to a measuring cylinder containing 100 mls of water. The cylinder was inverted through 180 degrees and back again for one full inversion, taking 2 seconds and the number of seconds for complete disintegration observed. The cylinder was then allowed to stand for 30 minutes, undisturbed, and a 10 ml sample taken from the centre of the cylinder and analysed, gravimetrically, for the amount of solids present. This figure was then used to calculate the % of material in suspension after standing for this time. The results were compared to two commercial formulations of Propanil, one (STAM® 80 EDF) manufactured by a standard extrusion technique involving the formulation of a paste and the other (WHAM® 80DF) by pan granulation. The results obtained were as follows:

| Commercial Product | Time Taken for Product to Disintegrate | % Remaining in Suspension after 30 minutes |
|---|---|---|
| Stam ® 80 EDF | 3–5 minutes | 71.3 |
| Wham ® 80 DF | >5 minutes | 8.9 |
| Example 1 | 1 minute | 86.9 |

The above results indicate the advantages of the product produced by the process described in this invention. In addition it was noted that the standard extruded product, Stam® 80 EDF was badly caked in the commercial pack, indicating a physical degradation of the product on storage.

EXAMPLE 2

The following formulation was prepared:

| | |
|---|---|
| Chlorsulfuron | 75% |
| Sodium alkyl aryl sulphonate | 1% |
| Sodium lignosulphonate | 12.5% |
| China Clay | to 100% |

The above formulation was prepared by first blending the Chlorsulfuron Technical and china clay in a Ploughshare blender for 5 minutes. The blend thus formed was then air milled to an average particle size of 3–4 microns. Water was added to the air milled premix in a Ploughshare blender until a water content of approx. 14.5% was obtained. Formation of a paste was avoided. The free-flowing powder was extruded in an extruder as described in WO96/26828. A compacted solid extrudate was obtained, which was dried at 60° C. for 15 minutes until a moisture content of 0.9% was obtained. The granules were tested by the method set out in Example 1.

The results were compared to a commercial formulation of chlorsulfuron, (GLEAN® 75 DF) manufactured by a standard fluid be agglomeration. The results obtained were as follows:

| Commercial Product | Time Taken for Product to Disintegrate | % Remaining in Suspension after 30 minutes |
|---|---|---|
| Glean ® 75 DF | <1 minute | 69 |
| Example 2 | <1 minute | 86 |

It was noted that the Glean® sample was much more dusty than the extruded sample produced by the process of the present invention. At the low use rate of the product, the higher susceptibility for the product would lead to a higher availability in field use and a higher efficacy.

The results were compared to a commercial formulation of chlorsulfuron. (GLEAN® 75 DF) manufactured by a standard fluid bed agglomeration. The results obtained were as follows:

| Commercial Product | Time Taken for Product to Disintegrate | % Remaining in Suspension after 30 minutes |
|---|---|---|
| Glean ® 75 DF | <1 minute | 69 |
| Example 2 | <1 minute | 86 |

It was noted that the Glean® sample was much more dusty than the extruded sample produced by the process of the present invention. At the low use rate of the product, the higher susceptibility for the product would lead to a higher availability in field use and a higher efficacy.

EXAMPLE 3

A commercial premix of Chloridazon 65 DF was obtained from which a commercial sample of water dispersible granule had been produced by a wet agglomeration technique.

The same premix was formed into granules using the process of the present invention and both samples were tested for suspensibility as set out in Example 1. The results obtained are as follows:

| | % Suspensibility |
|---|---|
| Commercial Chloridazon 65 DF | 89 |
| Example 3 | 98 |

EXAMPLE 4

The following formulation was prepared by a process according to the present invention:

| | |
|---|---|
| Captan | 80.0% |
| Sodium alkyl aryl sulphonate | 1.0% |
| Sodium naphthalene formaldehyde condensate | 2.0% |
| Silica | 3.0% |
| Kaolin | to 100% |

Zeta Potential Measurements may be used to evaluate the micro-electrophoretic mobility of active ingredient particles and accordingly derive the Zeta Potential of those particles. This allows preferred surfactants, in particular anionic, non-ionic and cationic dispersants, for water dispersible granules of the active ingredient to be selected so as to identify the most appropriate candidate dispersants. It is preferred that the dispersants give a Zeta Potential measurement of about 0 mV for a non-ionic surfactant and in excess of approximately −30 mV for an anionic surfactant and in excess of approximately +30 mV for a cationic surfactant.

The active material is suitably present at a level of at least 50%, preferably from 60 to 90% by weight of the granule. The excipient is suitably present at a level of less than 50%, preferably from 10 to 30% by weight of the granule. The liquid, preferably water, content of the granule is suitably less than 10% and preferably from 0.1 to 5% by weight of the granule.

What is claimed is:

1. A process for the production of water dispersible granules comprising, preparing a pre-mix in the form of a free-flowing powder comprising an active material and an excipient with at least one component of the pre-mixing being liquid, without forming a paste, feeding the pre-mix as a free-flowing powder to an extruder and extruding the pre-mix to form the water dispersible granules.

2. A process according to claim 1 in which a liquid is adsorbed onto an active solid material.

3. A process according to any one of the preceding claims in which the pre-mix is a homogeneous powder.

4. A process according to claim 1 in which the premix is formed by the application of shear.

5. A process according to claim 1 in which the pre-mix comprises an active material and an excipient selected from a surfactant, a filler, a disintegrant, a stabiliser, a flow aid and mixtures thereof.

6. A process according to claim 1 which comprises a preparing the pre-mix in a blending step and optionally in a milling step.

7. A process according to claim 6 in which the blending step is carried out for a period of at least 30 seconds.

8. A process according to claim 7 which comprises feeding the active material to a blending step, passing the blended material to a milling step so as to reduce the particle size of the blended material and passing the milled material to a further blending step to produce the pre-mix.

9. A process according to claim 8 in which the first blending step is conducted under conditions of high shear and the second blending step is conducted under conditions of low or moderate shear.

10. A process according to claim 9 in which the active material and an excipient selected from a disintegrant, a filler and a surfactant and mixtures thereof are blended in a blending step.

11. A process according to claim 10 in which a liquid and optionally a further excipient selected from a surfactant, a disintegrant and a filler are added to the process in a second or subsequent blending step.

12. A process according to claim 1 in which the liquid is added as a spray.

13. A process according to claim 1 which further comprises drying and optionally size classifying the extruded material.

14. A process according to claim 1 in which the active material is selected from, a pharmaceutical, an agricultural chemical, an oil field chemical, an animal feedstuff, a dyestuff, and a detergent.

15. A process according to claim 1 in which the active material is an agricultural chemical and is selected from, bensulfuron-methyl, captan, chloridazon, chlorsulfuron, glyphosate, oxyfluorfen and propanil.

16. A process according to claim 1 in which the pre-mix comprises a surfactant selected from alkyl aryl sulphonates, alkyl aryl sulphosuccinates, alkyl sulphates and lignosulphonates.

17. A process according to claim 1 in which the granule comprises propanil and excipients comprising an alkyl aryl sulphonate, a lignosulphonate, a disintegrant and a filter.

\* \* \* \* \*